United States Patent [19]

Blyakhman et al.

[11] 4,061,633

[45] Dec. 6, 1977

[54] METHOD OF RECOVERING PRIMARY AND SECONDARY AMINES

[76] Inventors: Lazar Isaevich Blyakhman, Krasnopresnensky val, 4/29, kv. 16; Sergei Lvovich Davydov, Tikhvinsky pereulok, 19, kv. 5a, both of Moscow; Valentina Fedorovna Kashina, Moskovskoe shosse, 4, kv. 45, Dolgoprudny Moskovskoi oblasti, all of U.S.S.R.

[21] Appl. No.: 445,633

[22] Filed: Feb. 25, 1974

[51] Int. Cl.² .......................................... C07D 295/02
[52] U.S. Cl. ............................. 544/106; 203/34; 203/49; 203/61; 260/293.51; 260/563 R; 260/583 R; 260/583 N; 260/583 P; 260/501.1; 544/178
[58] Field of Search ............... 260/582, 583 N, 247, 260/293.51, 563 R, 583 R, 583 P, 501.1, 567.6 R, 567.6 M, 514.5, 468 E; 203/61, 34, 49

[56] References Cited

U.S. PATENT DOCUMENTS

| | | | |
|---|---|---|---|
| 2,755,282 | 7/1956 | Hachmuth | 260/582 |
| 2,853,489 | 9/1958 | Moon | 260/582 |
| 3,072,662 | 1/1963 | Murray et al. | 260/582 |
| 3,131,221 | 4/1964 | Remes et al. | 260/583 N |
| 3,413,350 | 11/1968 | Cross et al. | 260/582 |
| 3,414,619 | 12/1968 | Cross et al. | 260/582 |
| 3,421,983 | 1/1969 | Buchsbaum | 203/98 |
| 3,725,210 | 4/1973 | Otsuka et al. | 203/49 |
| 3,783,147 | 1/1974 | Calicchia et al. | 260/583 N |

OTHER PUBLICATIONS

"Mass Transfer Operations", Treybal, McGraw-Hill, 1955, pp. 340 & 341.

*Primary Examiner*—Frank W. Lutter
*Assistant Examiner*—Frank Sever
*Attorney, Agent, or Firm*—Haseltine, Lake & Waters

[57] ABSTRACT

A method of recovering primary or secondary amines from aqueous, organic or aquo-organic solutions of said amines by subjecting these solutions to distillation or rectification in the presence of carbonic acid.

23 Claims, 1 Drawing Figure

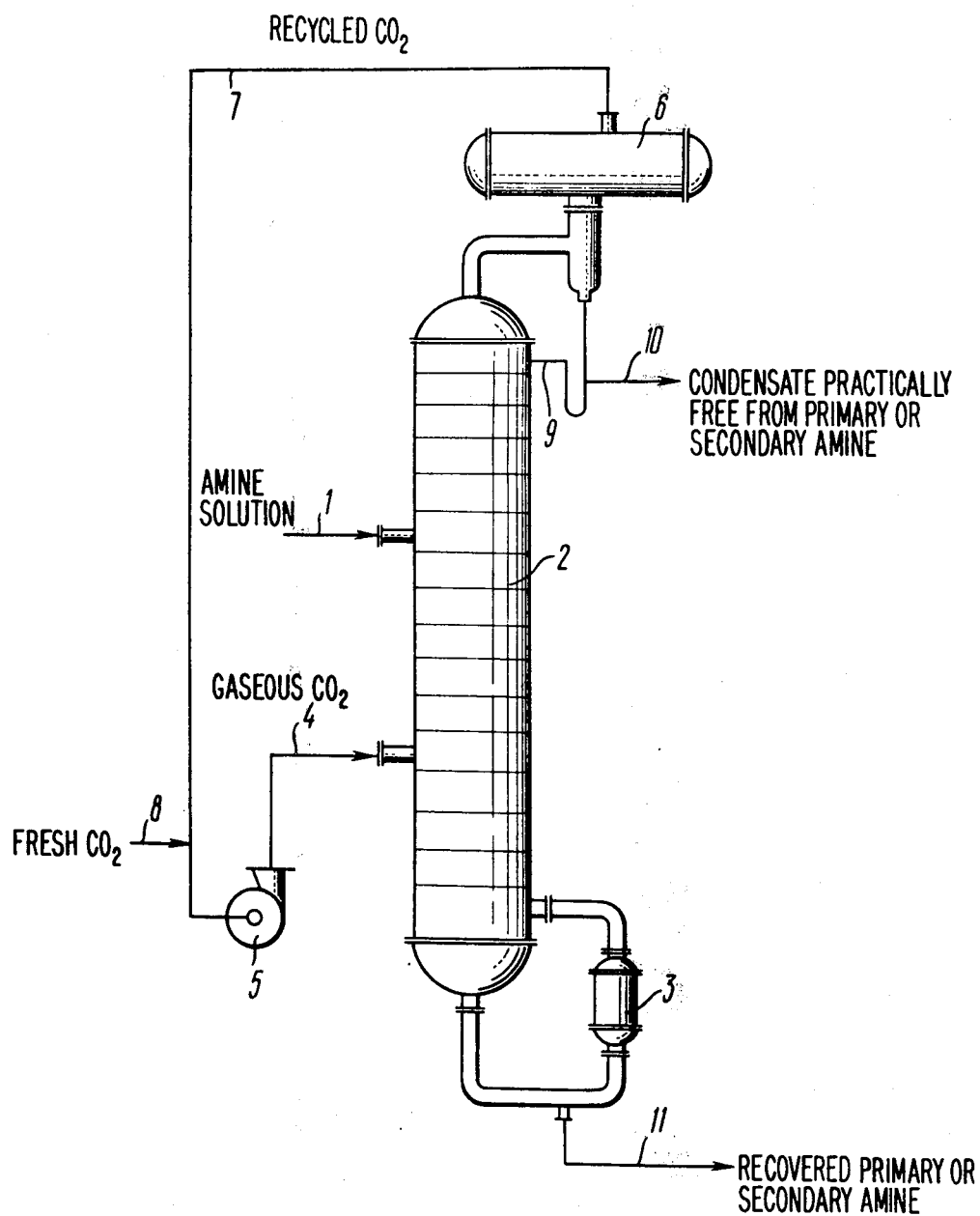

METHOD OF RECOVERING PRIMARY AND SECONDARY AMINES

The present invention relates to the field of chemical technology and, more specifically, to a method for recovering primary and secondary amines. The method of the present invention is useful for recovering primary and secondary aliphatic, heterocyclic, hydrogenated, aromatic, and other amines from aqueous or organic solutions including recovering from mixtures with tertiary amines. The method according to the present invention may be most preferably used for recovering primary and secondary amines having a $pK_a$ value (negative logarithm of the acidity constant) of at least 8.5.

The solution components may or may not form azeotropic mixtures with the amines being recovered.

The present invention makes it possible, in one of the particular embodiments thereof, to recover morpholine from aqueous solutions as well as from solutions containing, besides water, various N-alkylmorpholines.

Due to the existence of a very strong bond between water and a functional amino group, it is often difficult to recover an amine from an aqueous solution so as to obtain a good yield of the product. For example, the mixture water-morpholine may be regarded as a good illustration of the case; data of the equlibrium between liquid and vapor phases of the mixture show that the process of recovering morpholine from aqueous solutions by way of rectification is rather inefficient from the economic point of view, since it requires the use of cumbersome and expensive rectification columns and involves consumption of great amounts of heat, steam, and cooling water.

Substantial difficulties are encountered during separation of primary and secondary amines from tertiary ones due to a slight difference in boiling points or in azeotrope-formation temperatures. This may be exemplified by a sparingly separable system pyridine-piperidine which forms an azeotropic mixture containing 3.4 to 8% of pyridine when it is necessary to produce pure piperidine.

Moreover, various amines form azeotropic mixtures with water or organic substances. Thus, to separate an azeotropic mixture water - N,N'-diethylethylene diamine containing about 20% of the amine, a great energy consumption is required if water is to be distilled off azeotropically by way of introducing a third component; or, accordingly, great amounts of an extracting agent should be used if the amine is extracted from the aqueous solution; in this latter embodiment of the process, high values of energy consumption are not avoided due to regeneration of the extracting agent and isolation of the amine.

Such mixtures with a low amine content are frequently encountered in chemical processes where an amine is subjected to a series of transformations but the reaction does not proceed completely, wherefore there is a necessity to recover the amine and recycle it back into the process.

It is often advisable, in such processes, to concentrate an amine to a certain concentration thereof in a solution, but not to isolate it in its pure form.

Some methods have been proposed to cope with the above-mentioned problems. For instance, to recover an amine from an aqueous solution, it has been proposed to distill off water with a hydrocarbon forming an azeotropic mixture with water, said mixture having a minimal boiling point (cf. British Pat. No. 1,008,226). This method, however, also necessitates the use of cumbersome and expensive equipment and a great consumption of heat and cooling water, since great amounts of a solvent should be repeatedly evaporated.

To recover morpholine from aqueous solutions, there has been disclosed a method involving the use of a concentrated solution of caustic soda which strongly inhibits solubility of morpholine in water (U.S. Pat. No. 2,776,972). This prior art method also suffers a disadvantage residing in the necessity to regenerate caustic soda from diluted aqueous solutions. Such regeneration contemplates the use of an expensive equipment in combination with a great heat consumption.

To recover amines from aqueous solutions, there has been proposed a method of extraction, at elevated temperatures, with an inert organic solvent immiscible with water and unreactive with respect to the amine. Then, from the extract containing the solvent, amine and water, an azeotropic mixture of water with the solvent is first separated by rectification, whereafter the amine is recovered. Since the amine content in water is greater than in the solvent, the method implies the use of great amounts of the solvent; the amine recovery rate is insignificant.

It is an object of the present invention to provide a novel method of recovering primary and secondary amines which would not require the use of expensive equipment and increased heat consumption.

It is another object of the present invention to provide a method of recovering primary and secondary aliphatic, heterocyclic, hydrogenated aromatic, and other amines from aqueous or organic solutions thereof including solutions containing tertiary amines and substances forming azeotropic mixtures with the amines being recovered.

Still another object of the present invention is to provide a method of recovering morpholine from aqueous solutions and from solutions containing, in addition to water, N-alkylmorpholines and other organic compounds which would make possible the production of morpholine with a high purity grade.

These and other objects are accomplished in that in a method of recovering primary and secondary amines from aqueous, organic or aquo-organic solutions of said amines by way of distillation or rectification, according to the present invention said distillation or rectification is conducted in the presence of carbonic acid.

It is advisable to perform the method according to the present invention so that the rectification is effected while recycling carbonic acid within the system. It is also advisable to perform the method of the present invention in such a manner that said solutions are saturated with carbonic acid prior to the distillation or extraction.

The method of the present invention is based on the phenomenon that, as a result of reacting with carbonic acid, the volatility of primary and secondary aliphatic, heterocyclic and other amines is reduced, whereas the volatility of water and other organic substances remains unchanged and the solubility of amines in organic solvents is substantially decreased.

If the rectification of solutions containing amines is to be performed in the atmosphere of carbonic acid, the process may be conducted at operating reflux ratios which are much lower than minimal ones calculated from equilibrium curves; neither is it required to employ columns with a high resolution power.

In the rectification of azeotropic systems, an azeotropic mixture concentration is changed in the presence of carbonic acid, while in some cases an azeotropic mixture is not formed at all.

In the rectification process, an increase in the partial pressure of carbonic acid always results in a better separation efficiency and reduced minimal reflux ratios.

The method of recovering primary and secondary amines according to the present invention does not give any by-products, neither does it include any steps of chemical regeneration of an amine, while carbonic acid may be recycled back to the process by way of its circulation within the system.

The method of the present invention makes it possible to recover primary and secondary aliphatic, heterocyclic, hydrogenated aromatic, and other amines, especially those having a $pK_a$ value of at least 8.5, from aqueous and organic solutions of said amines as well as from solutions containing, in addition to water and amines, other organic liquids such as hydrocarbons and alcohols of the aliphatic, aromatic, alicyclic series; ethers of the aliphatic and aliphatic-aromatic series; tertiary amines of the aliphatic and heterocyclic series; heretocyclic compounds; nitro-compounds of the aromatic series, and the like.

The method according to the present invention is preferably embodied in the hereinbelow-described manner and is more fully apparent from the accompanying drawing schematically representing the flow-sheet of a continuous rectification process.

In this drawing, the starting solution containing a primary or secondary amine is supplied via a line 1 into a rectification column 2 provided with a boiler 3.

Into the same rectification column 2 gaseous carbonic acid is fed, below the inlet point of the starting solution, via line 4 by means of a gas-blower 5. After passing through the rectification column 2, the carbonic acid from a dephlegmator 6 is recycled back to the process via a line 7 and line 4 provided with the gas-blower 5. Fresh carbonic acid is introduced into the system via a line 8 for the compensation of its losses.

The vapors leaving column 2 along with carbonic acid are condensed in the dephlegmator 6.

The condensate is divided into two streams; the former is supplied via a line 9 for spraying of the column 2 as a reflux, while the latter is discharged via a line 10 as a distillate practically free from the primary or secondary amine but consisting of the components separated from the primary or secondary amines.

The separated primary or secondary amine is evacuated from the bottom portion of the rectification column 2 via a line 11; in doing so, an additional heating is performed, when appropriate, for a more complete separation of carbonic acid.

The rectification column 2 can operate both under atmospheric and reduced or superatmospheric pressure. Reflux ratios as well as resolving power of the column and ratios between the acid amount recycled through the column 2 and the amount of vapors being condensed in a time unit within the dephlegmator 6 ($G_{CO_2}/G_{vapors}$) may be selected based on economic considerations depending on the physical properties of the starting solution.

In some cases it is advisable, during separation of azeotropic mixtures, to perform the separation in the column 2 only partially and to discharge from its bottom portion not a pure amine but its concentrated solution, while from the top portion of the column 2 other components of the solution containing certain amounts of the amine should be evacuated.

Although a continuous rectification process described hereinabove is the most-preferred embodiment of the present invention, in some cases it is advisable to effect the separation using a periodically operating rectification column. In this case, the starting solution is charged into the column still and carbonic acid is recycled through the column. At first, other components of the solution are collected and then the acid recycling is discontinued; then the amine is discharged from the column still or, when required, from the dephlegmator after distillation.

Another embodiment of the method according to the present invention involves a pre-saturation of the solution to be separated with carbonic acid, followed by distillation or rectification performed in a continuous or discontinuous-action column in accordance with the above-described procedure under atmospheric pressure or vacuum, but without recycling carbonic acid through the rectification column.

For better understanding of the present invention, some specific Examples illustrating the method of recovering primary and secondary amines are given hereinafter.

EXAMPLE 1

Into a continuous action rectification column with carbonic acid being recycled within a closed system, an aqueous solution of morpholine is fed, the morpholine concentration being 20%. The column resolving power above the carbonic acid inlet point is 15 theoretical plates. At a ratio $G_{CO_2}/G_{vapor} = 1.8 - 2.5$ and the reflux ratio 0.5, there are obtained a distillate containing morpholine in an amount of up to 0.1% and liquid bottoms containing 99.2% of morpholine.

EXAMPLE 2

Into a continuous action column with the resolving power of its top portion of 15 theoretical plates a mixture of the following composition is fed: 48.4% of morpholine, 0.5% of ethanol, 1.2% of dioxane, 2.4% of methoxyethylamine, 4.6% of methylmorpholine 4.5% of ethylmorpholine, 1.8% of methylcellosolve (methyl ether of ethylene glycol) and 36.1% of water.

With continuous recycling of carbonic acid to ensure a ratio $G_{CO_2}/G_{vapor} = 1.8$ to 2.5 and the reflux ratio of 0.5, a distillate is obtained containing quantitatively all the components except morpholine which is contained in the distillate in an amount not exceeding 0.1%; the resulting liquid bottoms contain 99% of morpholine.

EXAMPLE 3

A 43.2% aqueous solution of cyclohexylamine (with the composition close to that of the azeotrope) is fed into a continuous action rectification column with the resolving power of 20 theoretical plates. During the rectification, carbonic acid is fed into the column. At a ratio $G_{CO_2}/G_{vapor} = 1.2 - 1.4$ and a reflux ratio of 0.3 to 0.5, a distillate containing up to 0.3% of the amine is discharged from the column top, while from a bottom cyclohexylamine with the concentration of 99.2% is discharged.

EXAMPLE 4

A solution with a composition close to the azeotropic and containing 48 wt.% of n-butylamine and 52 wt.% of ethanol is fed into a continuous action rectification column supplied with carbonic acid. The column resolving power above the acid inlet point is 15 theoretical plates.

At a ratio $G_{CO_2}/G_{vapor} = 1.0 - 1.2$ and the reflux ratio of 0.5, a distillate containing 0.6 wt.% of the amine and liquid bottoms containing 94.9 wt.% of the amine were obtained.

EXAMPLE 5

700 g of a solution containing 10.2% of methylmorpholine, 25.6% of morpholine and 64.2% of water are charged into the still of a discontinuous action rectification column with the resolving power of 35 theoretical plates. Carbonic acid is continuously supplied into the column so as to ensure the ratio $G_{CO_2}G_{vapor} = 1.1$. At the reflux ratio of 2 a distillate is obtained in the amount of 335 g containing 0.09% of morpholine and 21.3% of methylmorpholine; and another distillate is obtained in the amount of 202 g containing 9.4% of morpholine; the remaining product is liquid bottoms which after distillation give morpholine with a concentration of 98.6%.

EXAMPLE 6

650 g. of a solution containing 12.2% of ethylmorpholine, 26.1% of morpholine and 61.3% of water are charged into the still of a discontinuous action rectification column with the resolving power of 35 theoretical plates. The column is continuously supplied with carbonic acid. At the ratio $G_{CO_2}/G_{vapor} = 1.1$ and the reflux ratio of 2, 310 g of an aqueous distillate are obtained containing 0.083% of morpholine and 25.5% of ethylmorpholine, and 190 g of a distillate with a concentration of morpholine of 11.7%. From the liquid bottoms after distillation morpholine is obtained with a concentration of 98.2%.

EXAMPLE 7

475 g of an aqueous solution containing 10% of N,N'-diethylethylene diamine and 90% of water and saturated with carbon dioxide to a pH = 7.2 are subjected to fractional vacuum distillation (residual pressure 30 mm Hg) to yield a distillate; 164 g with an amine concentration of 0.045 wt.% and 197 g with an amine concentration of 0.46 wt.%; 20 g with an amine concentration of 4.8 wt.%; 51 g with an amine concentration of 8.8 wt.%. The remaining liquid bottoms contain 95.5 wt.% of the product.

EXAMPLE 8

100 g of a 30% solution of n-dibutylamine in o-xylene are saturated with carbon dioxide and then subjected to vacuum distillation (residual pressure 20 mm Hg, temperature about 50° C). After heating the evaporated solution to reflux under atmospheric pressure, 40 g of a 46.8% solution of n-dibutylamine in o-xylene are obtained.

EXAMPLE 9

A mixture of pyridine and piperidine of a near-to-azeotropic composition with a pyridine content of 4.1% is saturated with carbon dioxide and then subjected to a fractional distillation under the residual pressure of 50 mm Hg. After refluxing under atmospheric pressure piperidine is obtained in the bottoms in the amount of 85% of the starting mixture delivered to the distillation; this product contains practically no pyridine.

What is claimed is:

1. A method of concentrating a solution of an amine selected from the group consisting of primary amines and secondary amines, said amine having a $pK_a$ value equal to at least 8.5, in a solvent selected from the group consisting of water, an organic liquid other than a primary or secondary amine and mixtures of water and said organic liquid, wherein said solution is obtained from a crude reaction mass, and said organic liquid is a conventional diluent present within said crude reaction mass, said method comprising the steps of continuously distilling said solution of said amine in the presence of $CO_2$ in a rectification column, wherein the middle part of said column is supplied with said solution of said amine, the bottom part of said column is supplied with gaseous $CO_2$ and a mixture of $CO_2$ and vapors of said solvent are directed from the top part of the column to a cooler where the vapors of said solvent are condensed and a gaseous stream comprising $CO_2$ is recycled to the bottom part of said column; returning part of the condensed solvent vapors in said cooler in reflux form to said rectification column; recovering the remainder of said condensed solvent vapors free from said amine; and supplying the amine from the bottom part of said rectification column to a boiler where said amine is partly evaporated; directing the vapors of said amine from said boiler into the bottom part of said rectification column and withdrawing the part of the amine which has not evaporated from the bottom part of said rectification column and said boiler as the final product, said $CO_2$ functioning to reduce the volatility of the amine without affecting the volatility of the solvent.

2. A method as claimed in claim 1 wherein the amine is selected from the group consisting of morpholine, cyclohexylamine, n-butylamine, N,N'-diethyl ethylenediamine, n-dibutylamine and piperidine.

3. A method as claimed in claim 2, wherein the amine is morpholine.

4. The method of claim 1 wherein the organic liquid is selected from the group consisting of aliphatic, aromatic and alicyclic hydrocarbons and alcohols; aliphatic and aliphatic-aromatic ethers; aliphatic and heterocyclic tertiary amines; heterocyclic compounds other than amines; and nitroaromatic compounds.

5. The method of claim 1 wherein the amine is morpholine and the solvent is water.

6. The method of claim 1 wherein the amine is morpholine and the solvent is a mixture of N-alkylmorpholines.

7. A method of concentrating a solution of an amine selected from the group consisting of primary amines and secondary amines, said amine having a $pK_a$ value equal to at least 8.5, in a solvent selected from the group consisting of water, an organic liquid other than a primary or secondary amine and mixtures of water and said organic liquid, wherein said solution is obtained from a crude reaction mass, and said organic liquid is a conventional diluent present within said crude reaction mass, said method comprising the steps of charging said solution of said amine to a rectification still, passing gaseous $CO_2$ continuously through said still, heating said solution of said amine to boiling, condensing vapors of said solvent in a cooler, recycling a gaseous stream comprising $CO_2$ through said solution in said still, and separating said amine, free from said solvent, as bottoms from said still, said $CO_2$ functioning to reduce the volatility of the amine without affecting the volatility of the solvent.

8. A method as claimed in claim 7 wherein the amine is selected from the group consisting of morpholine cyclohexylamine, n-butylamine, N,N'-diethyl ethylenediamine, n-dibutylamine and piperidine.

9. A method as claimed in claim 8 wherein the amine is morpholine.

10. A method according to claim 7 wherein gaseous $CO_2$ is passed through said solution of said amine in said still, said solvent vapors are condensed under atmospheric or reduced pressure, and a gaseous stream comprising $CO_2$ is separated under superatmospheric pressure.

11. The method of claim 7 wherein the organic liquid is selected from the group consisting of aliphatic, aromatic and alicyclic hydrocarbons and alcohols; aliphatic and aliphatic-aromatic ethers; aliphatic and heterocyclic tertiary amines; heterocyclic compounds other than amines; and nitroaromatic compounds.

12. The method of claim 7 wherein the amine is morpholine and the solvent is water.

13. The method of claim 7 wherein the amine is morpholine and the solvent is a mixture of water and N-alkylmorpholines.

14. In the method of concentrating a solution of an amine selected from the group consisting of primary amines and secondary amines in a solvent selected from the group consisting of water, an organic liquid other than a primary or secondary amine and mixtures of water and said organic liquid wherein said amine has a $pK_a$ value of at least 8.5, by rectification in a rectification column having an overhead outlet, a bottoms outlet, and an amine solution inlet located between said overhead outlet and said bottoms outlet, wherein said solution is obtained from a crude reaction mass, and said organic liquid is a conventional diluent present within said crude reaction mass, the improvement comprising carrying out said rectification in the presence of a gaseous stream comprising $CO_2$ said $CO_2$ functioning to reduce the volatility of the amine without affecting the volatility of the solvent.

15. The method of claim 14 wherein said gaseous stream comprising $CO_2$ is continuously fed into said rectification column below said amine solution inlet and said amine is removed through said bottoms outlet.

16. The method of claim 15 wherein a gaseous stream comprising $CO_2$ is removed through said overhead outlet and recycled into said rectification column.

17. The method according to claim 15 wherein said amine is selected from the group consisting of morpholine, cyclohexylamine n-butylamine N,N'-diethylethylenediamine, n-dibutylamine, and piperidine.

18. The method of claim 14 wherein said amine solution is saturated with gaseous $CO_2$ prior to rectification.

19. The method according to claim 14 wherein said amine is selected from the group consisting of morpholine, cyclohexylamine, n-butylamine, N,N'-diethylethylenediamine, n-dibutylamine and piperidine.

20. In a method of concentrating a solution of an amine selected from the group consisting of primary and secondary amines in a solvent selected from the group consisting of water, an organic liquid other than a primary or secondary amine, and mixtures of water and said organic liquid wherein said amine has a $pK_a$ value of at least 8.5, by fractional distillation of said solution of said amine, wherein said solution is obtained from a crude reaction mass, and said organic liquid is a conventional diluent present within said crude reaction mass, the improvement comprising carrying out the distillation in the presence of gaseous $CO_2$ and separating said amine as bottoms and said solvent as overhead, said $CO_2$ functioning to reduce the volatility of the amine without affecting the volatility of the solvent.

21. The method according to claim 20 wherein said solution of said amine is saturated with $CO_2$ gas prior to distillation.

22. The method of claim 20 wherein the organic liquid is selected from the group consisting of aliphatic, aromatic and alicyclic hydrocarbons and alcohols; aliphatic and aliphatic-aromatic ethers; aliphatic and heterocyclic tertiary amines; heterocyclic compounds other than amines; and nitroaromatic compounds.

23. The method of claim 20 wherein the amine is piperidine and the solvent is pyridine.

* * * * *